(12) United States Patent
Kim

(10) Patent No.: US 12,185,939 B2
(45) Date of Patent: Jan. 7, 2025

(54) TROCAR SYSTEM FOR USE IN LAPAROSCOPIC SURGERY

(71) Applicant: Ki Seong Kim, Gyeonggi-do (KR)

(72) Inventor: Ki Seong Kim, Gyeonggi-do (KR)

(73) Assignee: Ki Seong Kim, Gyeonggi-do (KR)

( * ) Notice: Subject to any disclaimer, the term of this patent is extended or adjusted under 35 U.S.C. 154(b) by 598 days.

(21) Appl. No.: 17/612,141

(22) PCT Filed: Nov. 11, 2020

(86) PCT No.: PCT/KR2020/015740
§ 371 (c)(1),
(2) Date: Nov. 17, 2021

(87) PCT Pub. No.: WO2021/096207
PCT Pub. Date: May 20, 2021

(65) Prior Publication Data
US 2022/0225977 A1     Jul. 21, 2022

(30) Foreign Application Priority Data
Nov. 12, 2019   (KR) ........................ 10-2019-0144077

(51) Int. Cl.
*A61B 17/04*       (2006.01)
*A61B 17/34*       (2006.01)
*A61B 17/00*       (2006.01)

(52) U.S. Cl.
CPC ...... *A61B 17/0469* (2013.01); *A61B 17/0482* (2013.01); *A61B 17/34* (2013.01);
(Continued)

(58) Field of Classification Search
CPC . A61M 5/329; A61M 5/3291; A61B 17/0482; A61B 17/3403;
(Continued)

(56) References Cited

U.S. PATENT DOCUMENTS 4,553,543 A  * 11/1985  Amarasinghe ......... A61B 17/11
                                                606/153
5,176,691 A  *  1/1993  Pierce ................ A61B 17/0469
                                                606/144
(Continued)

FOREIGN PATENT DOCUMENTS

KR       20190017382 A  *  2/2019 ............. A61B 17/04

*Primary Examiner* — Brooke Labranche
*Assistant Examiner* — Mitchell Brian Hoag
(74) *Attorney, Agent, or Firm* — IP & T GROUP LLP

(57) ABSTRACT

Proposed is a trocar system for a laparoscopic surgery, the trocar system preventing improper suturing caused by shaking of the focus of a suturing needle during suturing of the peritoneal hole of the peritoneum after completion of a laparoscopic surgery, and including a suturing needle guide member having first and second suturing needle guide holes, a trocar unit detachably coupled to the suturing needle guide member and having third, fourth, fifth, and sixth suturing needle guide holes, a trocar to which the suturing needle guide member is detachably coupled and which is provided with seventh and eighth suturing needle guide holes, and a suturing needle provided with suturing thread guided through the first, third, fifth, and seventh suturing needle guide holes and second, fourth, sixth, and eighth suturing needle guide holes.

5 Claims, 16 Drawing Sheets

(52) U.S. Cl.
CPC ............... *A61B 2017/00477* (2013.01); *A61B 2017/00526* (2013.01); *A61B 17/0483* (2013.01); *A61B 17/3403* (2013.01)

(58) Field of Classification Search
CPC ........ A61B 2017/3445; A61B 17/0483; A61B 17/34; A61B 17/3401; A61B 2017/3413; A61B 17/3415; A61B 2017/3425; A61B 2017/3433; A61B 2017/3441; A61B 2017/345; A61B 2017/346; A61B 2017/347; A61B 2017/3482; A61B 2017/3492; A61B 17/00234; A61B 2017/3407; A61B 2017/3409; A61B 2017/3411; A61B 2017/3405; A61B 2017/3419; A61B 17/3421; A61B 17/3423; A61B 17/3417; A61B 2017/3427; A61B 2017/3429; A61B 17/3431; A61B 2017/3435; A61B 2017/3437; A61B 17/3439; A61B 2017/3443; A61B 2017/3447; A61B 2017/3449; A61B 2017/3452; A61B 2017/3454; A61B 2017/3456; A61B 2017/3458; A61B 17/3462; A61B 2017/3464; A61B 2017/3466; A61B 17/3468; A61B 17/3472; A61B 17/3474; A61B 17/3476; A61B 14/3478; A61B 2017/348; A61B 17/3494; A61B 17/3496; A61B 2017/3484; A61B 2017/3486; A61B 2017/349; A61B 2017/3488

USPC ......................................................... 606/148
See application file for complete search history.

(56) References Cited

U.S. PATENT DOCUMENTS

| | | | | |
|---|---|---|---|---|
| 6,258,106 | B1* | 7/2001 | Leonard | A61B 17/0469 606/144 |
| 6,599,297 | B1* | 7/2003 | Carlsson | A61F 11/202 604/174 |
| 6,755,844 | B2* | 6/2004 | Furusawa | A61B 17/12013 606/144 |
| 8,579,807 | B2* | 11/2013 | Moreno, Jr. | A61B 17/3462 600/203 |
| 10,105,161 | B2* | 10/2018 | Hendershot, III | A61M 13/003 |
| 10,327,761 | B2* | 6/2019 | Ho | A61B 17/0057 |
| 10,639,068 | B2* | 5/2020 | Parihar | A61B 17/0057 |
| 11,065,033 | B2* | 7/2021 | Kalhorn | A61B 17/1695 |
| 2012/0035623 | A1* | 2/2012 | Bagaoisan | A61B 17/0482 606/144 |
| 2014/0163323 | A1* | 6/2014 | Mohajer-Shojaee | A61B 17/0485 600/204 |
| 2015/0038793 | A1* | 2/2015 | Prior | A61M 5/329 600/204 |
| 2015/0038996 | A1* | 2/2015 | Malkowski | A61B 17/0483 606/148 |
| 2017/0079639 | A1* | 3/2017 | Mohajer-Shojaee | A61B 17/0218 |
| 2019/0000496 | A1* | 1/2019 | Shelton, IV | A61B 17/3417 |
| 2019/0142454 | A1* | 5/2019 | Kim | A61B 17/3421 604/164.01 |

\* cited by examiner

TROCAR SYSTEM FOR USE IN LAPAROSCOPIC SURGERY

This application is a national stage application of PCT/KR2020/015740 filed on Nov. 11, 2020, which claims priorities of Korean patent application number 10-2019-0144077 filed on Nov. 12, 2019. The disclosure of each of the foregoing applications is incorporated herein by reference in its entirety.

TECHNICAL FIELD

The present disclosure relates to a trocar system for laparoscopic surgery and, more particularly, to a trocar system for laparoscopic surgery that prevents improper suturing caused as a result of the focus of the suture needle being shaken when suturing the peritoneal hole of the peritoneum after completion of laparoscopic surgery.

BACKGROUND ART

In general, unlike conventional abdominal laparotomy, laparoscopic surgery is a surgical method in which four to six holes with a diameter of 0.5 to 1.2 cm are incised in the abdomen, a trocar with a diameter of 0.5 to 1.2 cm and a length of 15 to 16 cm is inserted to the hole, a light source and a camera are inserted through the hole of trocar after inserting a trocar, and various surgical instruments are inserted into the other hole to monitor the cutting, sewing, and molding of organs from the outside of the patient.

In order to perform laparoscopic surgery, it is known that a trocar is inserted into the patient's abdomen, a gas such as carbon dioxide gas is injected into the abdominal cavity to secure an intraperitoneal space, and then the operation area is performed while observing the surgical site using endoscopy and surgical instruments through a plurality of trocars.

When the operation is over, a suturing instrument is used to suture the surgical site. This suturing instrument seals the surgical site by holding the needle with fixed forceps inserted into the abdominal cavity through the trocar and stitching the surgical site. After sewing, opposite sides of the thread are pulled out of the body through a trocar to prevent the thread from coming loose, and a knot is made outside the body, and then the knot is pushed with a knot presser to form a knot in the abdominal cavity.

In this regard, patent document 1 discloses providing a trocar for laparoscopic surgery that is mounted through the peritoneum during laparoscopic surgery, has a hollow shape in which a space for guiding a camera or a surgical instrument into the abdominal cavity is formed therein, and a trocar housing that passes through the peritoneum, including: a hole-shaped first opening part formed on opposite sides of the upper end of the trocar housing and into which a suture needle connected with a suture thread is inserted; a second opening part in the shape of a slot formed on opposite sides of the lower end of the trocar housing and through which the suture needle passes along the longitudinal direction of the trocar housing; and a sealing member made of an elastic material to block the first opening part to prevent the leakage of carbon dioxide inside the trocar housing in a state in which the suture needle is inserted, and the lower end of the trocar housing has a structure cut in a diagonal direction.

However, in patent document 1, since the suture needle was not guided and applied in a wide area in the first opening part of the hole shape, there was a concern that the focus of the suture needle could be shaken.

In addition, due to the second opening part having a long length in the longitudinal direction of the slot shape, there was a concern that the focus of the suture needle could be shaken.

That is, when the suture needle passes through too close to the peritoneal hole, the peritoneal hole could be torn.

DOCUMENTS OF RELATED ART

Patent Document

Patent Document 1: Korean Utility Model Registration No. 20-0473904 (Registered on 2014 Jul. 31.)

DISCLOSURE

Technical Problem

Accordingly, the present disclosure has been made keeping in mind the above-mentioned problems occurring in the related art, and the present disclosure is intended to propose a trocar system for laparoscopic surgery that prevents improper suturing caused as a result of the focus of the suture needle being shaken when suturing the peritoneal hole of the peritoneum after completion of laparoscopic surgery.

Technical Solution

In order to achieve the above objective, the present disclosure provides a trocar system for laparoscopic surgery, including: a suture needle guide member in which through-holes interconnected to each other are formed in the outer surface of through-hole, and a first and second suture needle guide holes are formed to be elongated and inclined long in the longitudinal direction, respectively, at opposite sides of the outer surface on the periphery of the through-holes; a trocar which is detachably coupled to the suture needle guide member passes through the through-holes, has space is formed therein, in which a third and fourth suture needle guide holes facing the first and second suture needle guide holes are formed at one side of the outer surface passing through the through-hole while passing through the space, respectively, and a fifth and sixth suture needle guide holes facing the first and second suture needle guide holes are formed on the opposite side of the outer surface that does not pass through the through-hole, respectively; a trocar unit which is detachably coupled to the suture needle guide member, in which a through-hole passing through the trocar coupled to the suture needle guide member is formed on the outer surface, and the seventh and eighth suture needle guide holes facing the third and fourth suture needle guide holes are formed on one side of the outer surface close to one side of the trocar passing through the through-hole; and a suture needle provided with a suture thread that is guided to the first, third, fifth, seventh suture needle guide hole and the second, fourth, sixth, and eighth suture needle guide hole. Both the trocar coupled to the suture needle guide member and the trocar unit coupled to the suture needle guide member are inserted into the abdominal cavity of a patient to form a peritoneal hole while passing through the peritoneum. When the laparoscopic surgery is completed by the endoscope and surgical instrument inserted into the abdominal cavity of the patient through the through-hole while the trocar is separated from the suture needle guide member, the endoscope and surgical instrument is pulled out of the through-hole, the trocar is coupled to the suture needle guide member, and the peritoneal hole is sutured with a suture thread by guiding the suture needle to the first, third, fifth, and seventh suture needle guide holes and the second, fourth, sixth, and eighth suture needle guide holes.

Advantageous Effects

In the present disclosure, since the first and second suture needle guide holes are formed to be elongated and inclined long in the longitudinal directions of the guide part, there is an effect that the suture needle is guided while being applied in a wider area than in the prior art.

In addition, there is an effect that the suture needle is guided while being applied in the third, fourth, fifth, sixth suture needle guide hole of the trocar and the seventh, and eighth suture needle guide hole of the trocar over a wider area than in the prior art.

That is, there is an effect that the suture needle is stably fixed to the suture needle guide member, the trocar, and the trocar unit.

In other words, while preventing the focus of the suture needle from shaking compared to the prior art, the present disclosure has an effect of simultaneously preventing the peritoneal hole from being torn by penetrating too close to the peritoneal hole of the peritoneum.

According to the present disclosure, since the first and second guide parts of the first body are fitted into the first and second guide grooves of the second body, respectively, there is an effect of preventing the second body from shaking in the first body.

That is, the trocar system of the present disclosure has the effect of preventing the focus of the suture needle from shaking.

In addition, there is an effect that the first and second bodies can be easily coupled to each other and uncoupled from each other.

The present disclosure has the effect of preventing, by the stumbling block, the second body from being inserted too deeply into the through-hole of the first body.

That is, there is an effect of preventing a phenomenon in which the second body is not easily removed when the second body is required to be separated from the first body.

The present disclosure has the effect of further preventing the second body from shaking in the first body because the fitting protrusion of the elastic part is inserted into the fitting hole of the first body.

In addition, there is an effect of easily coupling and decoupling the fitting protrusion and the fitting hole due to the elasticity of the elastic part.

In the present disclosure, the fitting protrusion of the trocar is inserted into the fitting hole of the second body, so there is an effect of preventing the trocar from shaking in the sealing needle guide member.

That is, the trocar system of the present disclosure has the effect of preventing the focus of the suture needle from shaking.

In other words, according to the present disclosure, the fitting protrusion of the trocar is inserted into the fitting hole of the protrusion, so there is an effect of preventing the trocar from shaking in the suture needle guide member.

That is, the trocar system of the present disclosure has the effect of preventing the focus of the suture needle from shaking.

In addition, in the trocar system of the present disclosure, the protrusion is configured to protrude from the first body, so it is possible to confirm the coupling between the fitting hole of the protrusion and the fitting protrusion of the trocar from the outside.

That is, the trocar of the present disclosure is advantageous in that it can be confirmed that the trocar and the suture needle guide member are correctly coupled to each other, and at the same time, the centers of the first, third, fifth, and seventh suture needle guide holes and the second, fourth, sixth, and eighth suture needle guide holes coincide to insert the suture needle safely.

BEST MODE

Accordingly, an embodiment of the present disclosure as described above will be described in detail with reference to the accompanying drawings.

Figure 1:
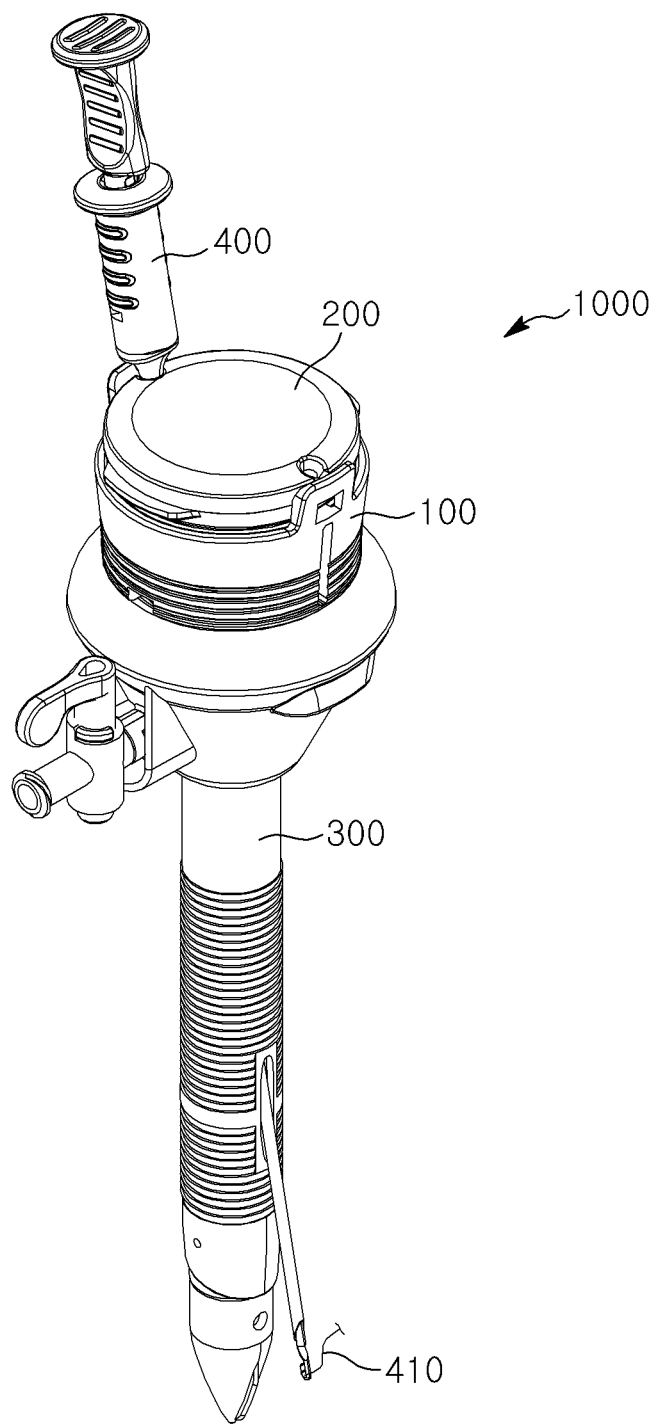
FIGS. 1 and 2 are a combined perspective view, and an exploded perspective view of a trocar system for laparoscopic surgery according to an embodiment of the present disclosure.
Figure 2:
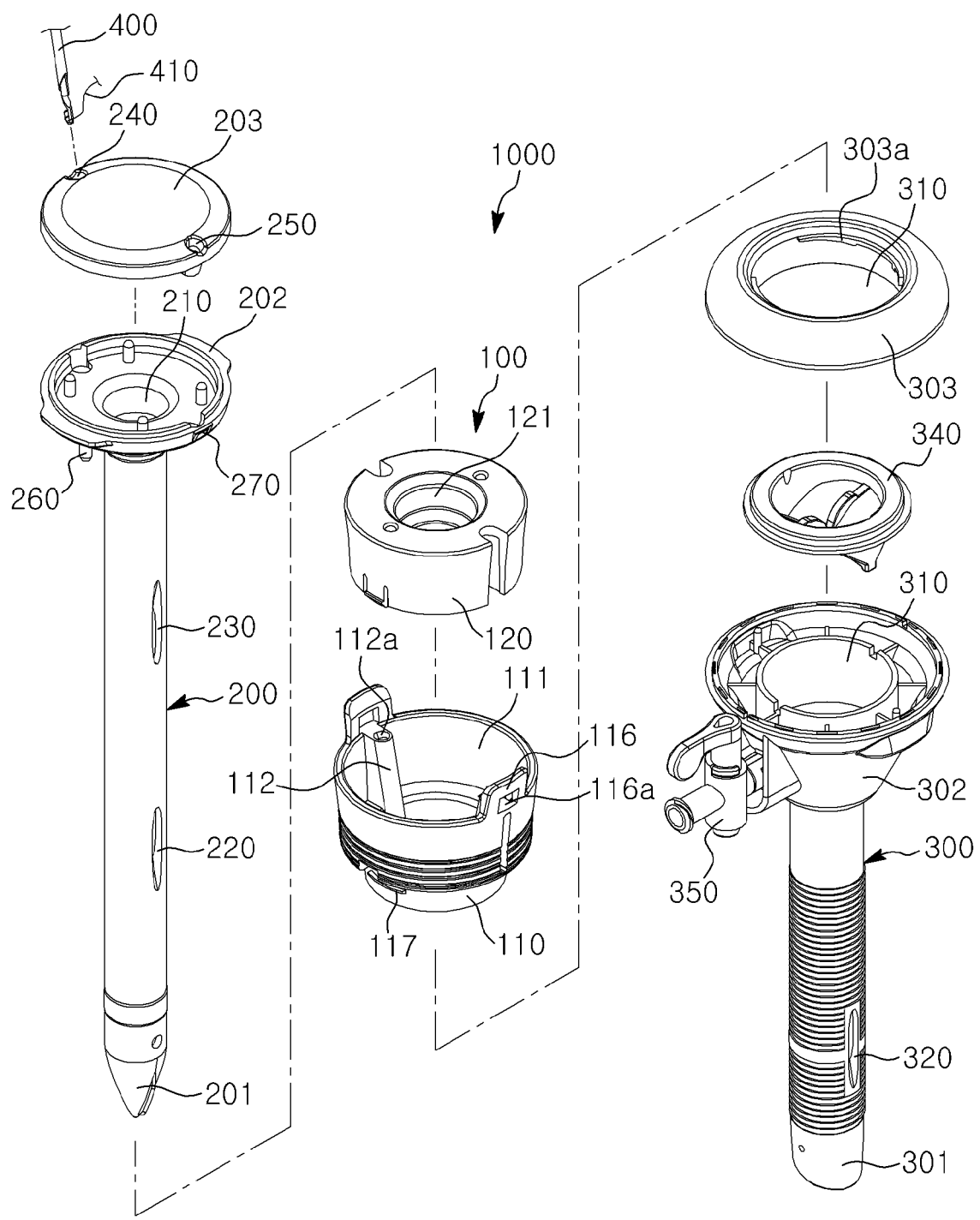
Figure 3A:
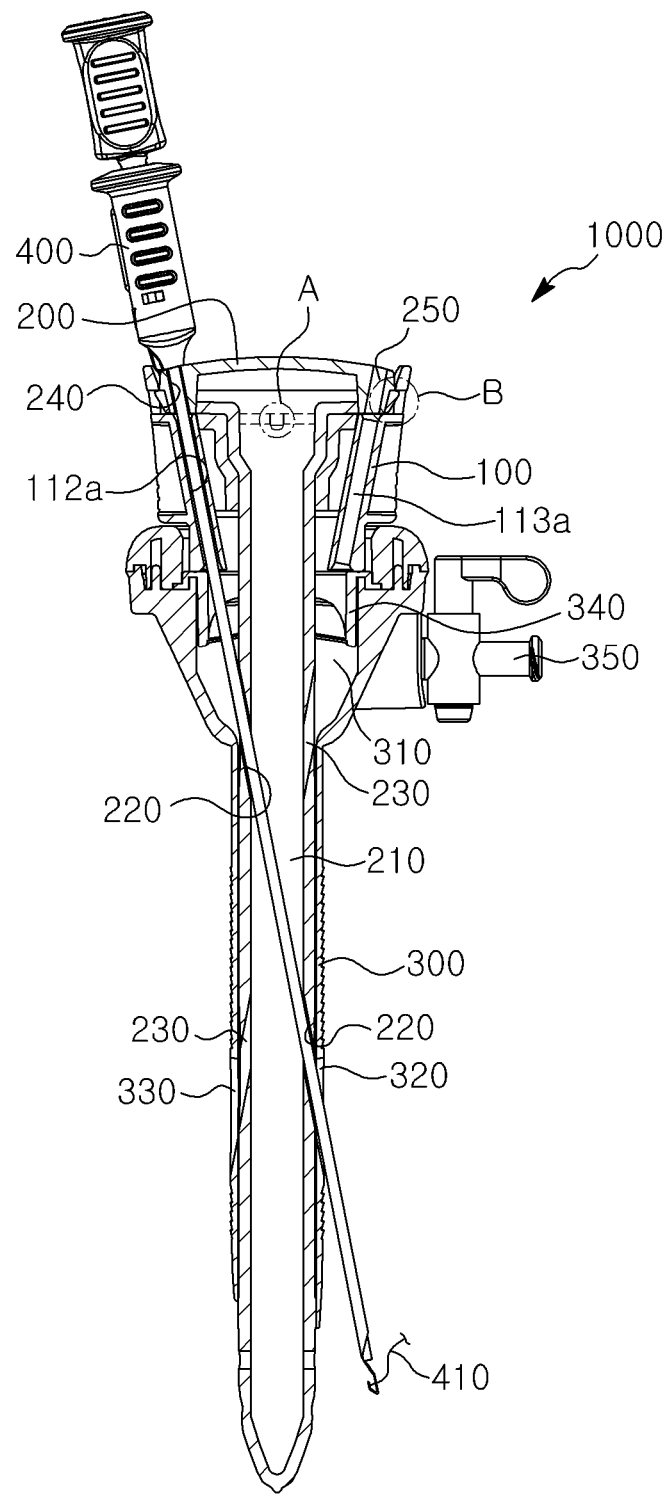
FIGS. 3A to 3c are a cross-sectional views of a trocar system for laparoscopic surgery according to an embodiment of the present disclosure.
Figure 3B:
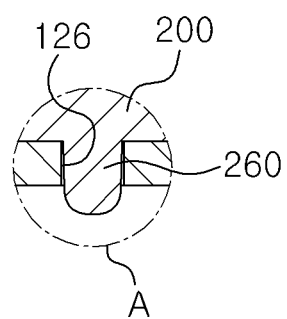
Figure 3C:
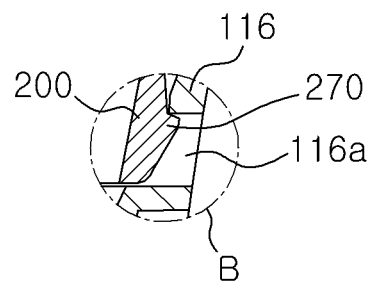
Figure 4:
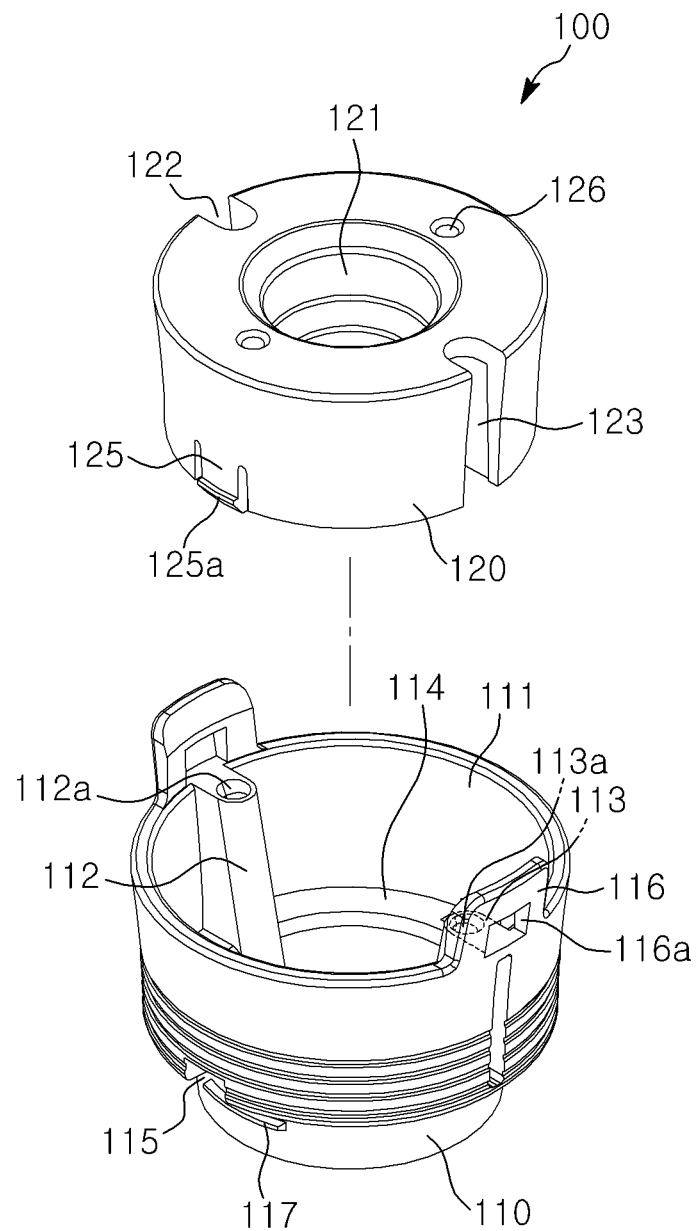
FIGS. 4 to 12 are detailed views of a trocar system for laparoscopic surgery according to an embodiment of the present disclosure.
Figure 5:
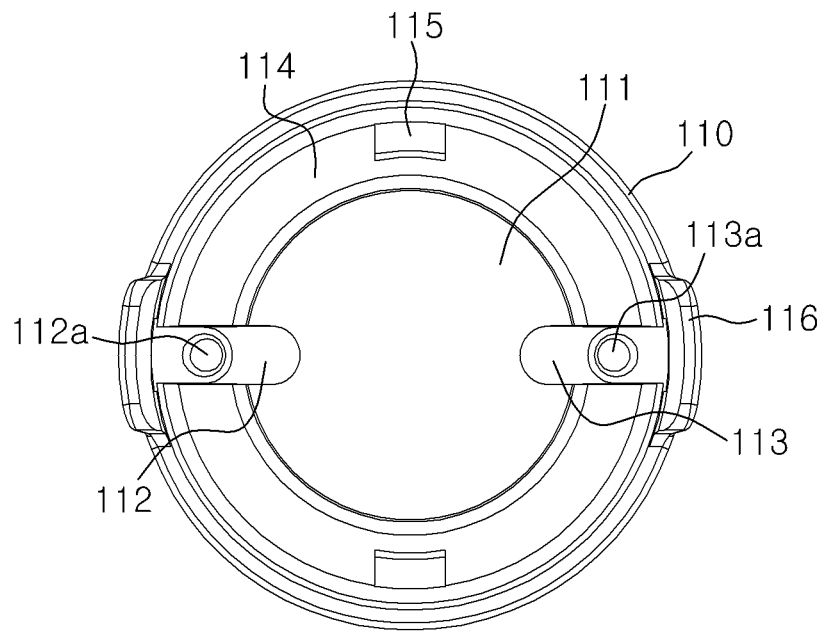
Figure 6:
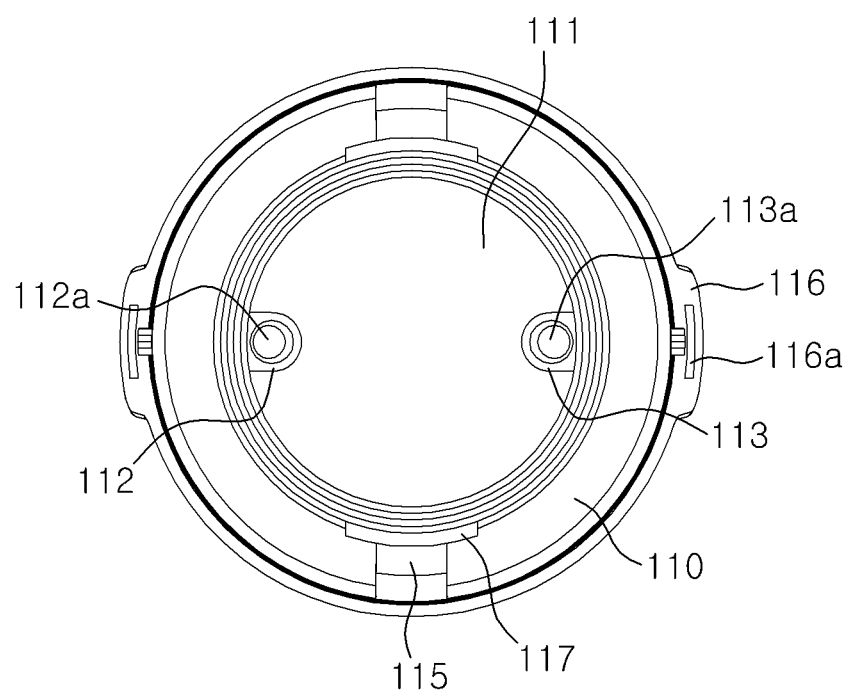
Figure 7:
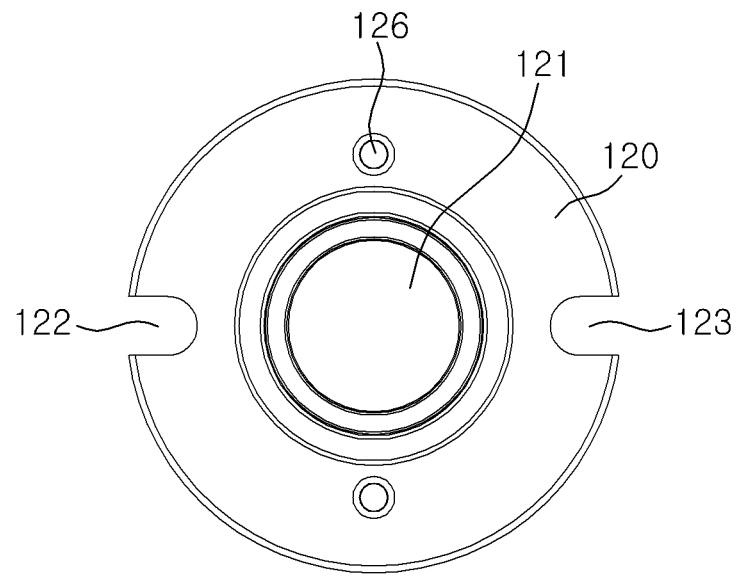
Figure 8:
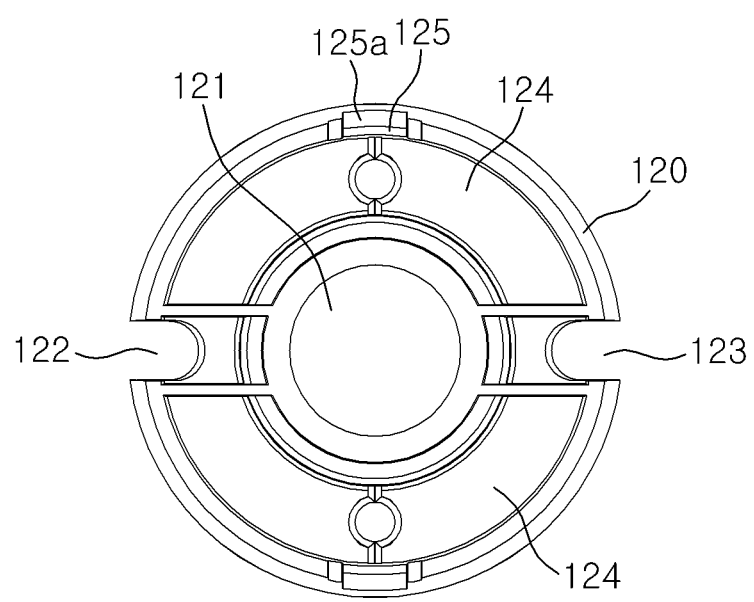
Figure 9A:
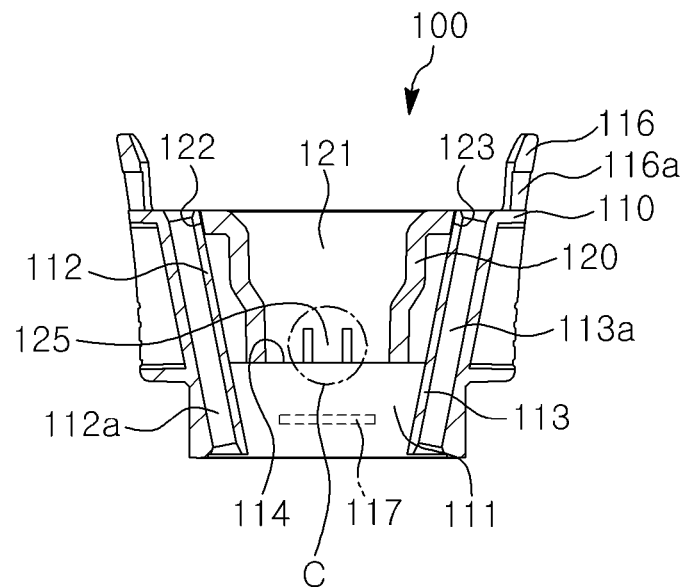
Figure 9B:
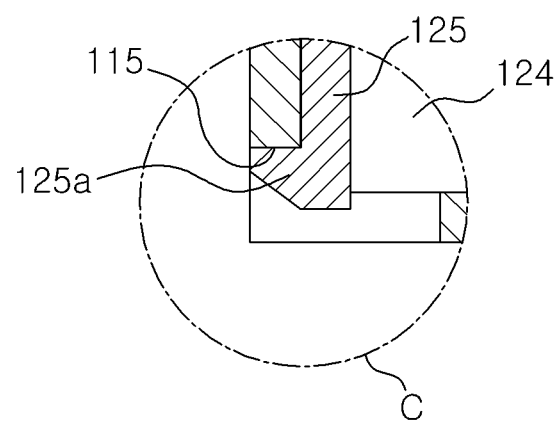
Figure 10:
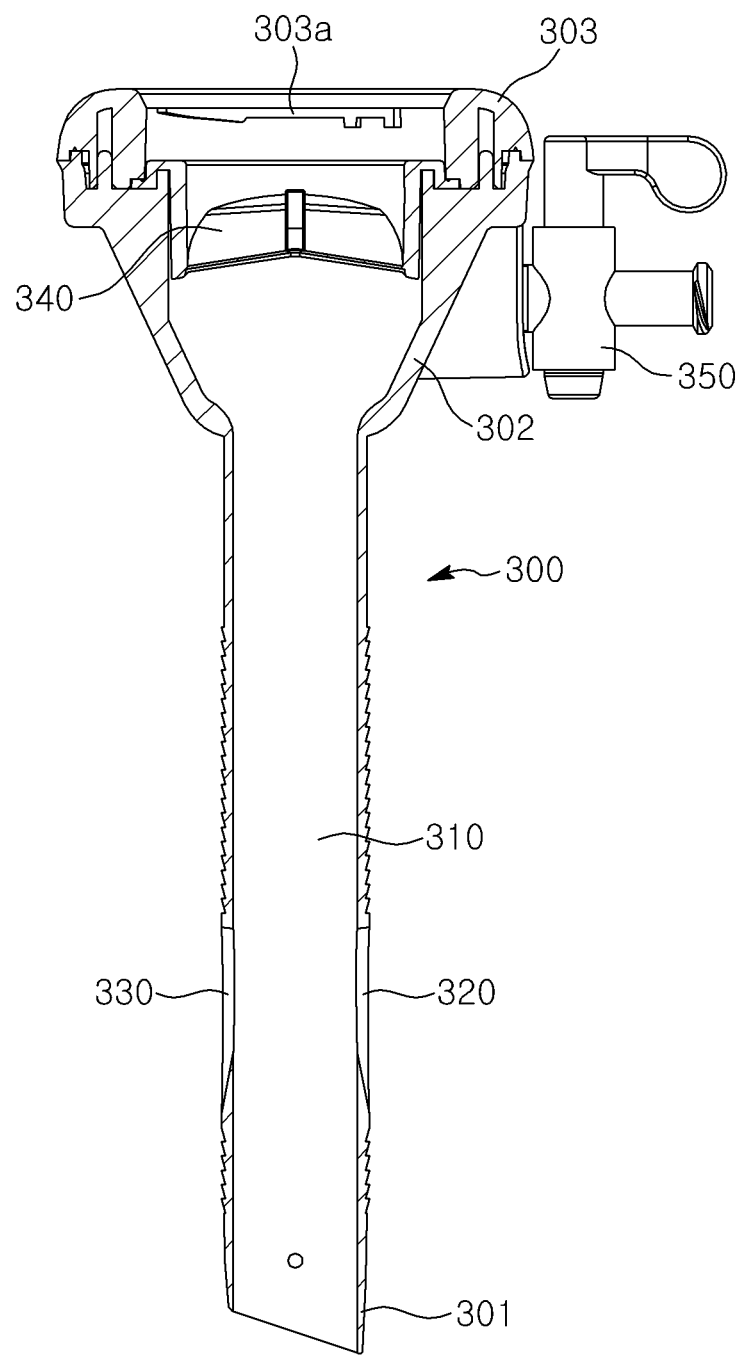
Figure 11:
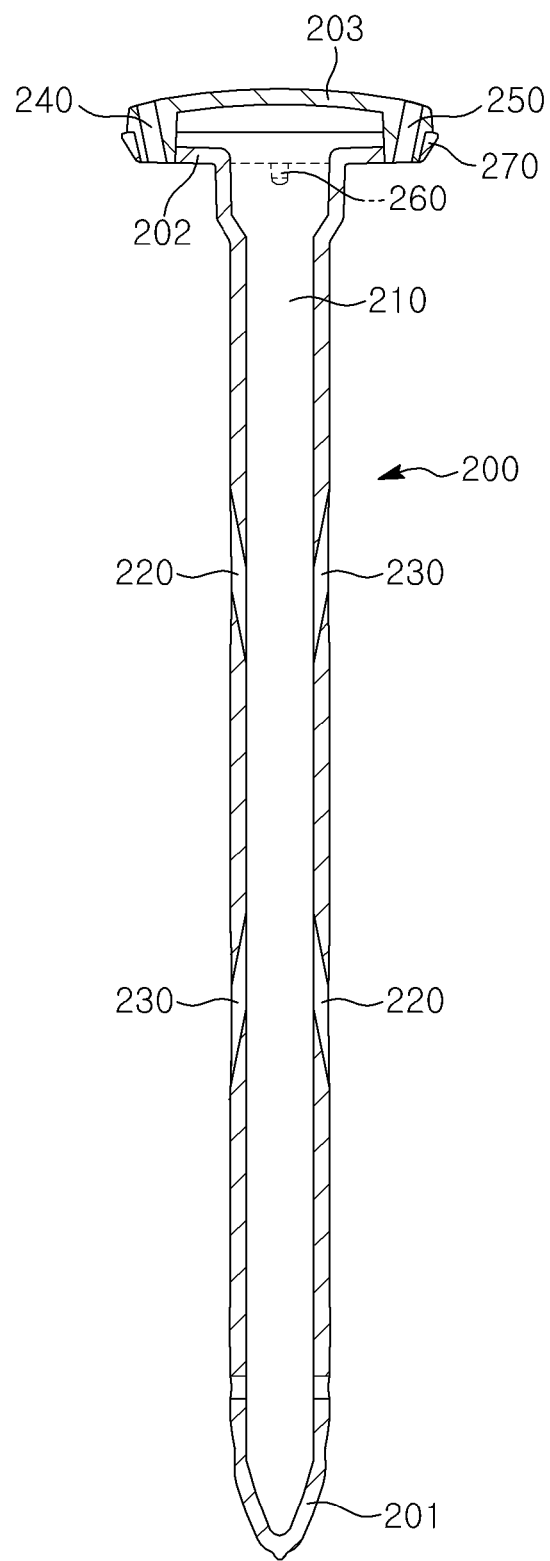
Figure 12:
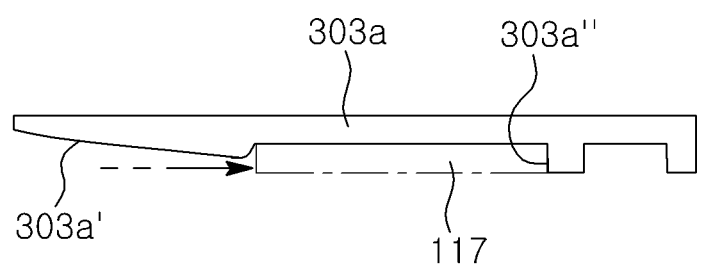
Figure 13:
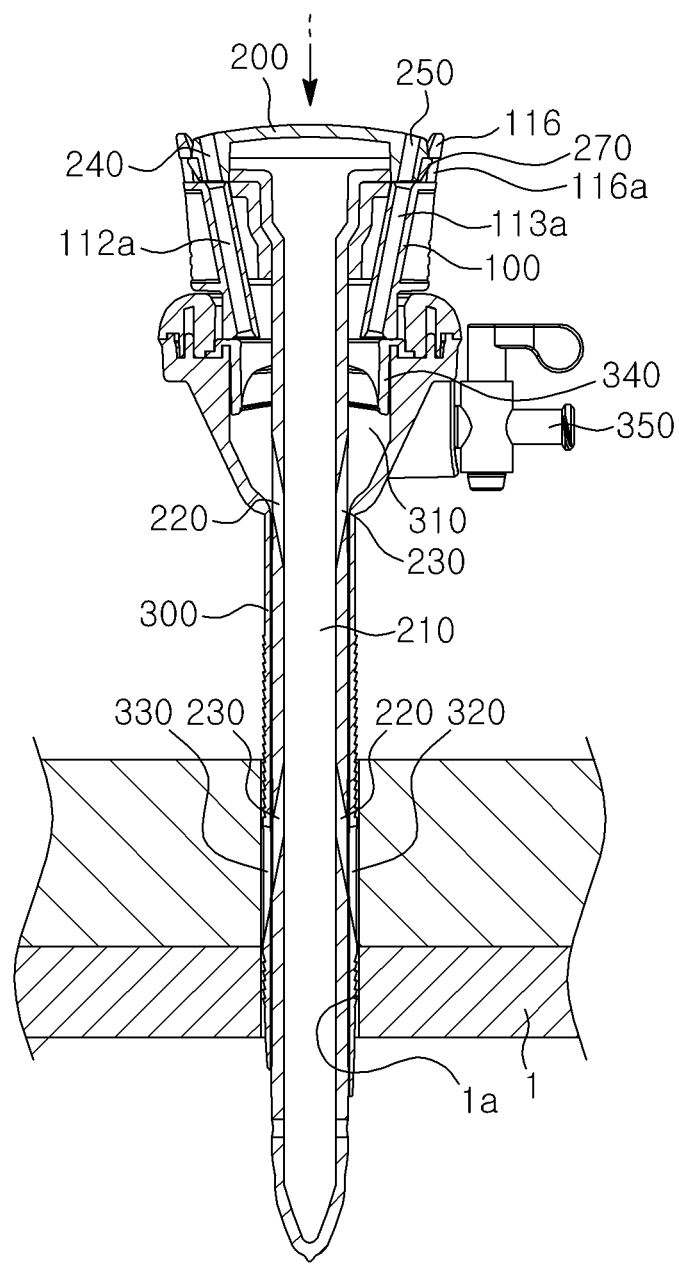
FIGS. 13 to 17 are views of a state of use of a trocar system for laparoscopic surgery according to an embodiment of the present disclosure.
Figure 14:
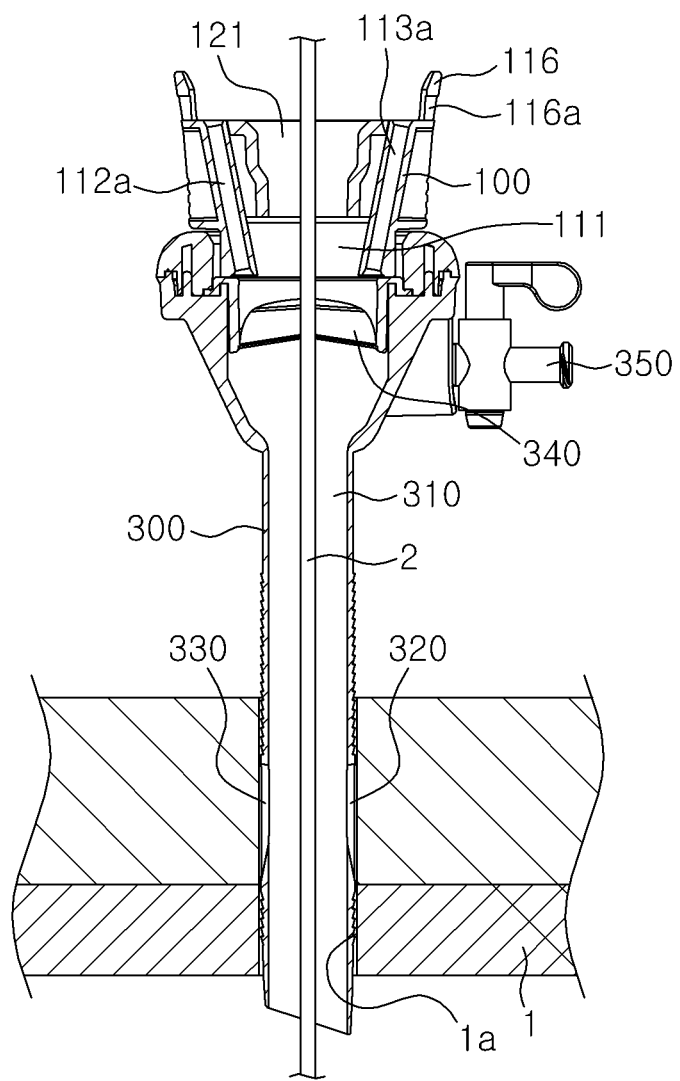
Figure 15:
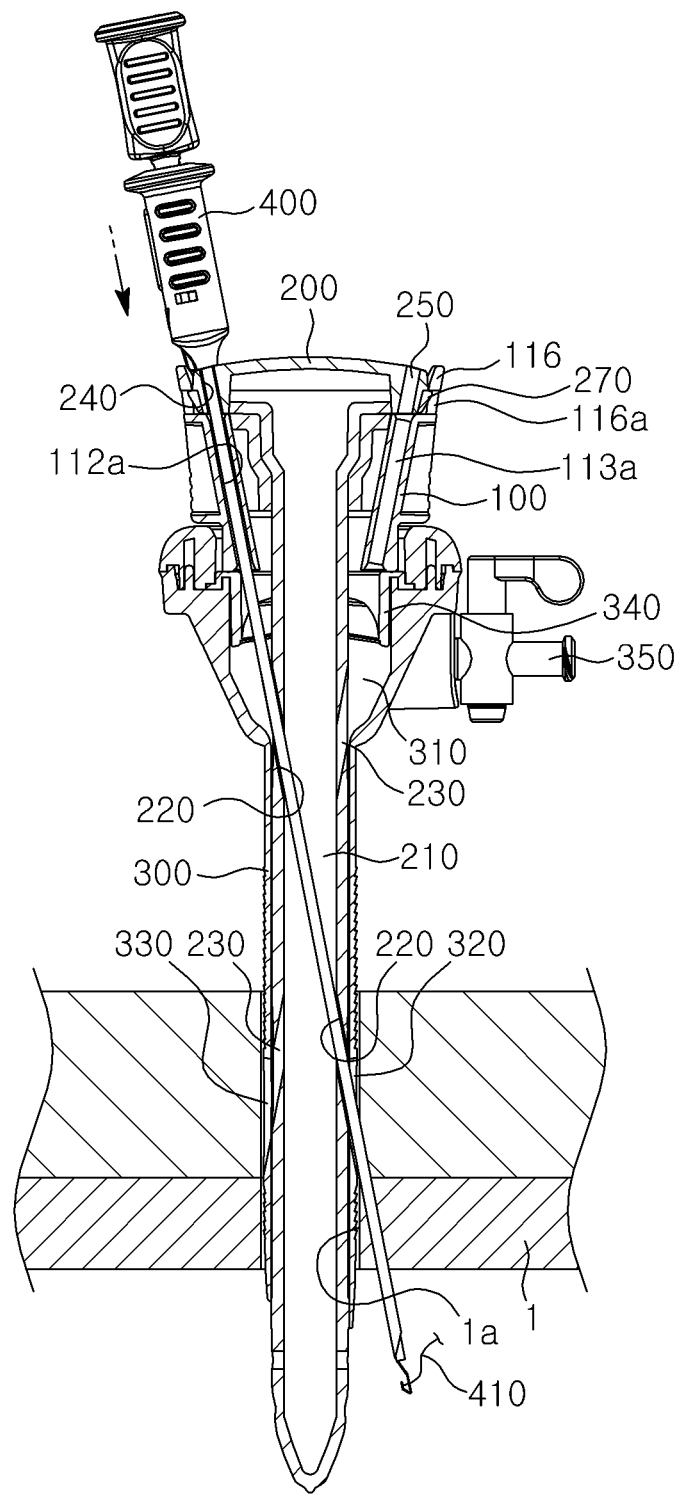
Figure 16:
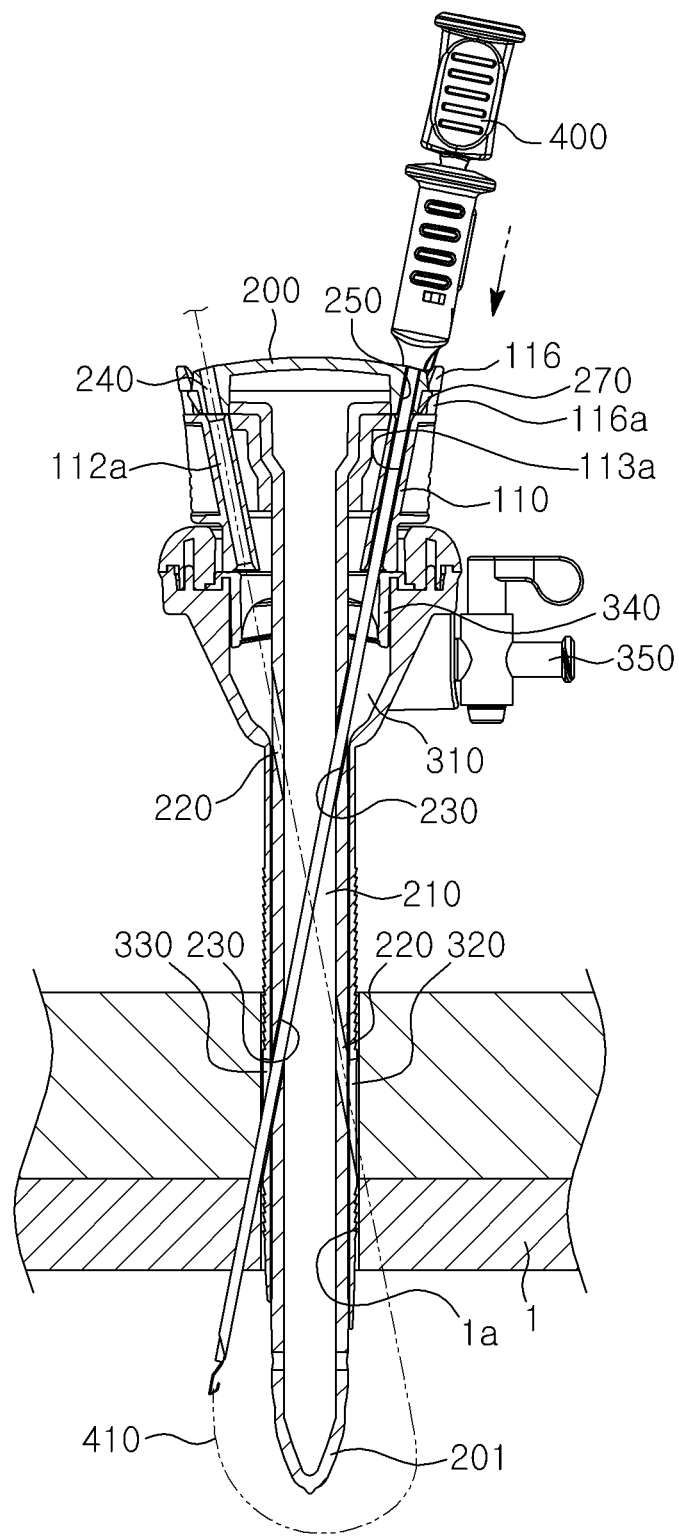
Figure 17:
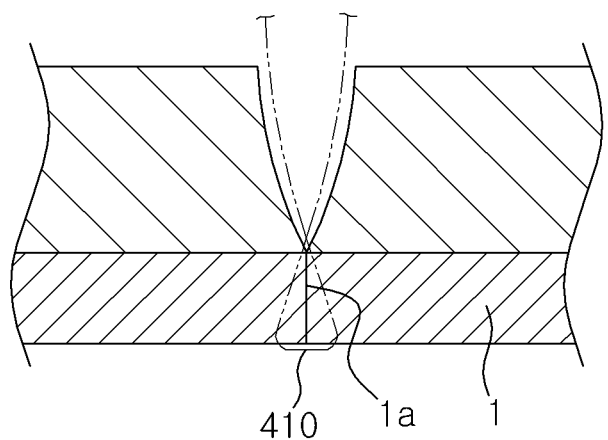

As shown in FIGS. 1 to 17, the trocar system 1000 for laparoscopic surgery according to an embodiment of the present disclosure includes a suture needle guide member 100, which has interconnected through-holes 111 and 121 formed at the outer surface thereof, and the first and second suture needle guide holes 112a and 113a on the periphery of the through-holes at opposite sides of the outer surface, and are formed to be elongated and inclined in longitudinal directions on the outer surfaces of the through-hole 111 and 121, respectively.

The trocar system 1000 for laparoscopic surgery includes a trocar 200 which is detachably coupled to the suture needle guide member 100 and passes through the through-holes 111 and 121, has a space 210 is formed therein, in which the third and fourth suture needle guide holes 220 and 230 facing the first and second suture needle guide holes 112a and 113a are formed at one side of the outer surface passing through the through-hole 111 and 121 while passing through the space 210, respectively. The fifth and sixth suture needle guide holes 240 and 250 facing the first and second suture needle guide holes 112a and 113a are formed on the opposite side of the outer surface that does not pass through the through-holes 111 and 121, respectively.

The trocar system 1000 for laparoscopic surgery includes a trocar unit 300, which is detachably coupled to the suture needle guide member 100, in which a through-hole 310 passing through a trocar 200 coupled to the suture needle guide member 100 is formed at the outer surface thereof, and the seventh and eighth suture needle guide holes 320 and 330 facing the third and fourth suture needle guide holes 220 and 230 are formed on one side of the outer surface of the trocar unit 300 close to one side of the trocar passing through the through-hole 310.

The trocar system 1000 for laparoscopic surgery includes a suture needle 400 equipped with a suture thread 410 guided to the first, third, fifth, and seventh suture needle guide holes 112a, 220, 240, and 320, and the second, fourth, sixth, and eighth suture needle guide holes 113a, 230, 250, and 330.

Here, a traction part for pulling and releasing the suture thread 410 is formed at the end of the suture needle 400.

In addition, the suture needle guide member 100 includes a first body 110 which is detachably coupled to trocar unit 300, in which a through-hole 111 is formed in the center of the outer surface, and the first and second guide parts 112 and 113 are formed to protrude in longitudinal directions on opposite sides of the inner surface of the through-hole 111, respectively. The first and second suture needle guide holes 112a and 113a are formed to be elongated and inclined in the longitudinal directions on the outer surface of the first and second guide parts 112 and 113.

Here, a stumbling block 114 is formed on the inner surface of the through-hole 111.

In addition, at least one fitting hole 115 connected to the through-hole 111 is formed on the outer surface of the first body 110.

Here, the fitting hole 115 is formed on opposite sides of the through-hole 111, respectively.

In addition, a protrusion 116 having a fitting hole 116a around the first and second suture needle guide holes 112a and 113a is formed to protrude on one side of the first body 110 to which the trocar 200 is blocked.

In addition, at least one fastening part 117 is formed to protrude from one outer surface of the first body 110 inserted into the through-hole 310 of the trocar unit 300.

The suture needle guide member 100 includes a second body 120 to which the trocar 200 is detachably coupled, in which the suture needle guide member 100 is inserted into the through-hole 111, the through-hole 121 connected to the through-hole 111 is formed in the center of the outer surface, and the first and second guide grooves 122 and 123 into which the first and second guide parts 112 and 113 are inserted while being guided to the first and second guide parts 112 and 113 are formed on opposite outer surfaces of the through-hole 121, respectively.

Here, a space 124 is formed between the first and second guide grooves 122 and 123 by opening one side of the second body 120 around the through-hole 121 on one side of the second body 120 in which the through-hole 121 is formed.

In addition, at least one elastic part 125 is formed on the outer surface of the second body 120 by cutting a part of the open inlet of the space 124.

Here, the elastic parts 125 are respectively formed on opposite sides of the through-hole 121.

In addition, a fitting protrusion 125a to be fitted into the fitting hole 115 is formed to protrude from the outer surface of the elastic part 125.

Here, the elastic part 125 has elasticity as a part of the open inlet of the space 124 is cut to opposite sides of the fitting protrusion 125a.

In addition, at least one fitting hole 126 is formed around the through-hole 121 at one side of the second body 120 to which the trocar 200 is blocked.

Here, the fitting hole 126 is formed on opposite sides of the through-hole 121 in a direction perpendicular to the first and second guide grooves 122 and 123.

In addition, the second body 120 is inserted into the through-hole 111 and is blocked by the stumbling block 114.

A fitting protrusion 260 fitted into the fitting hole 126 is formed to protrude from the outer surface of the trocar 200, and a fitting protrusion 270 fitted into the fitting hole 116a is formed to protrude.

In addition, the trocar 200 has a space 210, and the third and fourth suture needle guide holes 220 and 230 are formed therein, includes a through part 201 passing through the peritoneum 1; and a handle part 202 formed on one side of the through part 201, in which a fitting protrusion 260 and 270 are formed on an outer surface thereof, and a protrusion and a hole are formed on an inner surface thereof.

Here, the hole is formed passing through the handle part 202.

In addition, the trocar 200 includes a protrusion of the handle part 202 and a handle cover 203 in which a hole and a protrusion to which the hole is fitted are formed on the outer surface.

Here, the fifth and sixth suture needle guide holes 240 and 250 are formed passing through the protrusion of the handle cover 203.

Furthermore, the trocar unit 300, in which a through-hole 310 and the seventh and eighth suture needle guide holes 320 and 330 are formed, includes a through part 301 passing through the peritoneum 1; and a handle part 302 formed on one side of the through part 301, in which a through-hole 310 is formed in the center, and a protrusion and a hole are formed around the through-hole 310.

In addition, the trocar unit 300 includes a handle cover 303 in which a through-hole 310 is formed in the center, and a protrusion of the handle part 302 and a hole and a protrusion fitted into the hole are formed on the outer surface around the through-hole 310.

Here, a fastening part 303a for fastening with the fastening part 117 of the first body 110 is formed to protrude on the inner surface of the through-hole 310.

In addition, the fastening part 303a is formed longer in the circumferential direction than the fastening part 117 of the first body 110, and a guide surface 303a' is formed on one side of the outer surface that comes into contact at first when the fastening part 117 is fastened. A fitting groove 303a'' into which the fastening part 117 guided to the guide surface 303a' is fitted and fixed is formed on one side opposite the outer surface.

Furthermore, the trocar unit 300 includes a check valve 340 that is installed between the handle part 302 and the handle cover 303 and prevents the gas inside the abdominal cavity from flowing out through the through-hole 310 to the outside.

Here, the check valve 340 is passed through by the suture needle 400.

The trocar unit 300 is formed with a handle part 302, in which a gas supply/discharge part 350 having a valve for injecting and discharging medical gas into the abdominal cavity is connected to the through-hole 310.

The operation of the present disclosure configured as described above is as follows.

As shown in FIGS. 1 to 17, the trocar system 1000 for laparoscopic surgery, according to an embodiment of the present disclosure, combines the first and second bodies 110 and 120 of the suture needle guide member 100.

In more detail, the first and second guide parts 112 and 113 of the first body 110 are guided to the first and second guide grooves 122 and 123 of the second body 120 are fitted obliquely.

Here, the elastic part 125 of the second body 120 is bent and elastically deformed into the space 124 while the fitting protrusion 125a is applied on the inner surface of the through-hole 111. When the elastic part 125 is reached to the fitting hole 115 of the first body 110, the fitting protrusion 125a is returned to its original state by elasticity, and the fitting protrusion 125a is fitted into the fitting hole 115.

In addition, the second body 120 is fitted into the through-hole 111 while being blocked on the stumbling block 114 of the first body 110.

Then, after coupling the suture needle guide member 100 to the trocar unit 300, the trocar 200 is coupled to the suture needle guide member 100.

Here, the fitting protrusion 260 of the trocar 200 is fitted into the fitting hole 126 of the suture needle guide member 100.

In addition, the fitting protrusion 270 of the trocar 200 is fitted into the fitting hole 116a of the suture needle guide member 100.

In addition, the first, third, fifth, and seventh suture needle guide holes 112a, 220, 240, and 320 are aligned with the centers in the diagonal direction, and the second, fourth, sixth, and eighth suture needle guide holes 113a. 230, 250, and 330 are also aligned with the centers in the diagonal direction opposite to the diagonal direction.

That is, the trocar 200 is stably fixed to the trocar unit 300 through the suture needle guide member 100 and passes through the through-holes 111 and 121 of the suture needle guide member 100, and the through-hole 310 of the trocar 310.

Then, the trocar unit 300 and the trocar 200 are inserted into the abdominal cavity through the incision in which the skin of a patient is cut in advance to pass through the peritoneum 1.

Here, a peritoneal hole 1a is formed at the peritoneum 1.

Then, after separating the trocar 200 from the suture needle guide member 100, the endoscope and surgical instrument 2 is inserted into the abdominal cavity through the through-holes 111, 121, and 310 of the suture needle guide member 100 and the trocar unit 300 to start laparoscopic surgery.

Here, the inside of the abdominal cavity is expanded due to the medical gas supplied through the gas supply/discharge unit 350 of the trocar unit 300 to form an operating space.

In addition, the trocar unit 300 fitted into the peritoneal hole 1a maintains the shape of the peritoneal hole 1a.

After the laparoscopic surgery is completed, the endoscope and the surgical instrument 2 is taken out from the inside of the abdominal cavity.

Then, the trocar 200 is coupled to the suture needle guide member 100.

Then, the first, third, fifth, and seventh suture needle guide holes 112a, 220, 240, and 320 are aligned with the centers in the diagonal direction, and the second, fourth, sixth, and eighth suture needle guide holes 113a. 230, 250, and 330 are also aligned with the centers in the diagonal direction opposite to the diagonal direction.

Then, after moving the seventh and eighth suture needle guide holes 320 and 330 of the trocar unit 300 to a position for suturing the peritoneal hole 1a, the suture needle 400 provided with a suture thread 410 is guided to the first, third, fifth, and seventh suture needle guide holes 112a, 220, 240, and 320 to pass through the periphery of the peritoneal hole 1a.

Here, since the first suture needle guide hole 112a is formed to be elongated and inclined long in the longitudinal direction of the first guide part 112, the suture needle 400 is guided while being applied in a wide area.

In addition, since the suture needle 400 is guided to the third and fifth suture needle guide holes 220 and 240 of the trocar 200 and the seventh suture needle guide hole 320 of the trocar unit 300, the suture needle 400 is more efficiently guided by applying over a wide area.

Then, in the traction part of the suture needle 400 located inside the abdominal cavity, the suture thread 410 is grabbed with forceps of another auxiliary trocar system to release the traction, and then the suture thread 410 is moved from the position where the suture thread 410 was located to the opposite position.

Then, the suture needle 400 from which the suture thread 410 is separated is withdrawn from the first, third, fifth, and seventh suture needle guide holes 112a, 220, 240, and 320.

Here, the suture thread 410 remains inserted into the first, third, fifth, and seventh suture needle guide holes 112a, 220, 240, and 320.

Then, the suture needle 400 is guided to the second, fourth, sixth, and eighth suture needle guide holes 113a, 230, 250, and 330 to pass through the periphery of the peritoneal hole 1a.

Here, since the second suture needle guide hole 113a is formed to be elongated and inclined long in the longitudinal direction of the second guide part 113, the suture needle 400 is guided while being applied in a wide area.

In addition, since the suture needle 400 is guided to the fourth and sixth suture needle guide holes 230 and 250 of the trocar 200 and the eighth suture needle guide hole 330 of the trocar unit 300, the suture needle 400 is more efficiently guided while being applied in a wide area.

Then, the suture thread 410 is pulled while fixing the suture thread 410 with the traction part of the suture needle 400 and discharged to the outside through the second, fourth, sixth, and eighth suture needle guide holes 113a, 230, 250, and 330.

Here, the suture thread 410 remains inserted into the first, second, third, fourth, fifth, sixth, seventh, and eighth needle guide holes 112a, 113a, 220, 230, 240, 250, 320, and 330.

Then, while pulling out the trocar unit 300 from the peritoneal hole 1a, the suture thread 410 is removed from the first, second, third, fourth, fifth, sixth, seventh, and eighth needle guide holes 112a, 113a, 220, 230, 240, 250, 320, and 330, and then the peritoneal hole 1a of the peritoneum 1 is sutured with the suture thread 410 knot.

Here, the medical gas in the abdominal cavity is discharged through the gas supply/discharge unit 350 of the trocar unit 300.

On the other hand, after releasing the coupling between the fitting hole 115 and the fitting protrusion 125a by elastically deforming the elastic part 125 with an external force, the coupling of the first and second bodies 110 and 120 may be released by pulling the first and second guide parts 112 and 113 out from the first and second grooves 122 and 123.

In the above, although an exemplary embodiment of the present disclosure has been described for illustrative purposes, those skilled in the art will appreciate that various modifications, additions and substitutions are possible, without departing from the scope and spirit of the disclosure as disclosed in the accompanying claims.

DESCRIPTION OF THE REFERENCE NUMERALS IN THE DRAWINGS

100: suture needle guide member
110: first body
111: through-hole
112: first guide part
112a: first suture needle guide hole 113: second guide part
113a: second suture needle guide hole
114: stumbling block
115: fitting hole
116: protrusion
116a: fitting hole
120: second body
121: through-hole
122: first guide groove
123: second guide groove
124: space
125: elastic part
125a: fitting protrusion
126: fitting hole
200: trocar
210: space
220: third suture needle guide hole
230: fourth suture needle guide hole
240: fifth suture needle guide hole
250: sixth suture needle guide hole
260: fitting protrusion
270: fitting protrusion
300: trocar unit
310: through-hole
320: seventh suture needle guide hole
330: eighth suture needle guide hole
400: suture needle
410: suture thread
1000: trocar system for laparoscopic surgery

The invention claimed is:

1. A trocar system for use in laparoscopic surgery, the trocar system comprising:
    a suture needle guide member in which first and second through-holes interconnected to each other are formed, and first and second suture needle guide holes are formed as two elongated lumens inclined at different angles and formed, respectively, at opposite sides of the suture needle guide member;
    a trocar, which is detachably coupled to the suture needle guide member and which passes through the first and second through-holes of the suture needle guide member, the trocar having a space therein, the trocar having third and fourth suture needle guide holes facing the first and second suture needle guide holes of the suture needle guide member and formed at one side of an outer surface of the trocar that passes through the first and second through-holes of the suture needle guide member while passing into the space of the trocar; and
    the trocar having fifth and sixth suture needle guide holes facing the first and second suture needle guide holes of the suture needle guide member formed at an opposite side of the outer surface of the trocar, the fifth and sixth suture needle guide holes do not pass through the first and second through-holes of the suture needle guide member
    a trocar-containing unit, which is detachably coupled to the suture needle guide member, having a central through-hole through which the trocar passes, wherein the central through-hole of the trocar-containing unit is formed around the outer surface of the trocar, and the trocar-containing unit having seventh and eighth suture needle guide holes facing the third and fourth suture needle guide holes of the trocar and formed on one side of an outer surface of the trocar-containing unit adjacent the side of the trocar passing through the first and second through-holes of the suture needle guide member; and
    a suture needle provided with a suture thread that is guided through the first, third, fifth, and seventh suture needle guide holes and then through the second, fourth, sixth, and eighth suture needle guide holes;
    wherein the trocar coupled to the suture needle guide member and the trocar-containing unit coupled to the suture needle guide member are configured to be inserted into an abdominal cavity of a patient to form a peritoneal hole while passing through a peritoneum, and when a laparoscopic surgery is completed by an endoscope and surgical instrument inserted into the abdominal cavity of the patient through the through-holes while the trocar is separated from the suture needle guide member, the endoscope and surgical instrument are configured to be pulled out of the first and second through-holes of the suture needle guide member and the trocar is then coupled to the suture needle guide member, and the peritoneal hole is configured to be sutured with a suture thread by guiding the suture needle through the first, third, fifth, and seventh suture needle guide holes and then through the second, fourth, sixth, and eighth suture needle guide holes;
    wherein the suture needle guide member comprises:
    a first body, which is detachably coupled to the trocar-containing unit, having first and second guide parts formed to be elongated and to protrude in longitudinal directions on opposite sides of an inner surface of the first through-hole of the first body, respectively, and the first and second suture needle guide holes elongated and inclined in the longitudinal directions comprise the lumens on outer surfaces of the first and second guide parts; and
    a second body which is inserted into the central through-hole of the trocar-containing unit and detachably coupled to the trocar, in which the central through-hole of the trocar-containing unit is connected to the second through-hole formed in a center of the second body, and the second body has first and second guide grooves into which the first and second guide parts are inserted while being guided to the first and second guide parts, the first and second guide grooves formed respectively on opposite sides of the outer surface of the second through-hole formed in the center of the second body.

2. The trocar system of claim 1, wherein a stumbling block, by which the second body inserted into the through-hole of the trocar-containing unit is blocked, is formed in the inner surface of the first through hole of the first body.

3. The trocar system of claim 1, wherein at least one fitting hole connected to the first through-hole of the first body is formed on the outer surface of the first body,
    a space is formed between the first and second guide grooves by opening one side of the second body around the second through-hole formed in a center of the second body, and
    at least one elastic part is formed on the outer surface of the second body by cutting a part of an open inlet of the space, and a fitting protrusion configured to be fitted into the fitting hole is formed to protrude from an outer surface of the elastic part.

4. The trocar system of claim 1, wherein at least one fitting hole is formed around the second through-hole at one side of the second body by which the trocar is blocked, and
    a fitting protrusion configured to be fitted into the fitting hole protrudes from the outer surface of the trocar.

5. The trocar system of claim 1, wherein a protrusion having a fitting hole around the first and second suture needle guide holes is formed to protrude on one side of the first body by which the trocar is blocked, and a fitting protrusion fitted into the fitting hole is formed to protrude on the outer surface of the trocar.

* * * * *